United States Patent [19]

Krämer et al.

[11] Patent Number: 5,354,779

[45] Date of Patent: Oct. 11, 1994

[54] SUBSTITUTED OXIME ETHER AMIDES

[75] Inventors: Wolfgang Krämer, Burscheid; Dieter Berg, Wuppertal; Heinz-Wilhelm Dehne, Monheim; Stefan Dutzmann, Hilden; Christoph Erdelen, Leichlingen, all of Fed. Rep. of Germany

[73] Assignee: Bayer Aktiengesellschaft, Leverkusen, Fed. Rep. of Germany

[21] Appl. No.: 983,984

[22] Filed: Nov. 30, 1992

[30] Foreign Application Priority Data

Dec. 9, 1991 [DE] Fed. Rep. of Germany ....... 4140558

[51] Int. Cl.⁵ .............................................. A01N 37/20
[52] U.S. Cl. .................................. 514/619; 514/237.5; 514/241; 514/354; 514/396; 514/621; 514/640; 544/168; 544/218; 546/326; 548/131; 548/341.1; 548/376.1; 564/167; 564/169
[58] Field of Search ................ 564/256, 258, 265, 167, 564/169; 514/640, 619, 621, 237.5, 241, 354, 396

[56] References Cited

FOREIGN PATENT DOCUMENTS

| | | |
|---|---|---|
| 0370629 | 5/1990 | European Pat. Off. |
| 0398692 | 11/1990 | European Pat. Off. |
| 464381 | 1/1992 | European Pat. Off. |
| 3220524 | 1/1982 | Fed. Rep. of Germany |
| 1096037 | 12/1967 | United Kingdom |

OTHER PUBLICATIONS

Chemical Abstracts, vol. 95, vol. 34, No. 4, (1981) pp. 765-786.
Chemical Abstracts, vol. 102, vol. 24, No. 4, (1985) pp. 639-646.
Tetrahedron Letters, vol. 23, No. 36, (1982) pp. 3699-3702.

*Primary Examiner*—Richard L. Raymond
*Assistant Examiner*—Brian M. Burn
*Attorney, Agent, or Firm*—Sprung Horn Kramer & Woods

[57] ABSTRACT

New oxime ether amides of the formula (I)

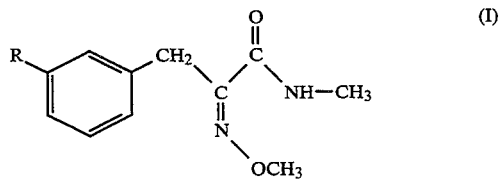

in which R has the meaning given in the description, and a plurality of processes for their preparation were described.

The new oxime ether amides are used as pesticides.

4 Claims, No Drawings

SUBSTITUTED OXIME ETHER AMIDES

The invention relates to new substituted oxime ether amides, to a process for their preparation, and to their use as pesticides.

It has been disclosed that certain substituted acrylic ester derivatives such as, for example, the compound methyl 3-methoxy-2-(2-methylphenyl)-acrylate or the compound methyl 3-methoxy-2-(2-phenoxyphenyl)-acrylate, have fungicidal properties (compare, for example, EP 178, 826).

However, the activity of these previously known compounds is not entirely satisfactory in all fields of application, in particular when low amounts and concentrations are applied.

New substituted oxime ether amides of the general formula

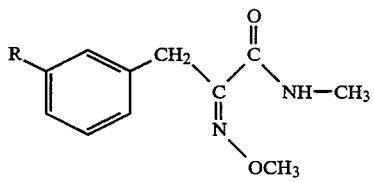
(I)

in which
R represents optionally substituted aryl or a radical of the formula

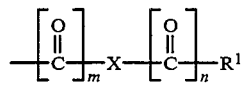

where
R¹ represents alkyl, halogenoalkyl, alkoxyalkyl or alkoxycarbonylalkyl, or represents in each case optionally substituted cycloalkyl, cycloalkylalkyl, aryl, arylalkyl, heterocyclyl or heterocyclylalkyl,
X represents oxygen or a radical of the formula N—R²,
R² represents hydrogen or alkyl,
m represents a number 0 or 1 and
n represents a number 0 or 1,
have been found.

Depending on the nature of the substituents, the compounds of the formula (I) may exist in the form of geometric and/or optical isomers or mixtures of isomers of various compositions. The invention claims the pure isomers as well as the mixtures of isomers.

It has furthermore been found that the new substituted oxime ether amides of the general formula (I)

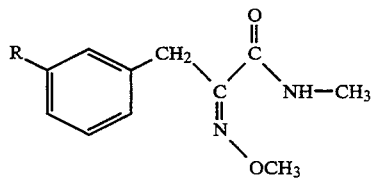
(I)

in which
R represents optionally substituted aryl or a radical of the formula

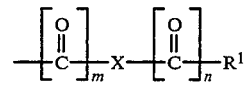

where
R¹ represents alkyl, halogenoalkyl, alkoxyalkyl or alkoxycarbonylalkyl, or represents in each case optionally substituted cycloalkyl, cycloalkylalkyl, aryl, arylalkyl, heterocyclyl or heterocyclylalkyl,
X represents oxygen or a radical of the formula N—R²,
R² represents hydrogen or alkyl,
m represents a number 0 or 1 and
n represents a number 0 or 1,
are obtained when
a) acrylide derivatives of the formula (II)

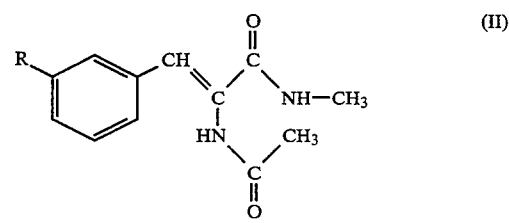
(II)

in which
R has the abovementioned meaning
are reacted with an acid addition salt of O-methylhydroxylamine, if appropriate in the presence of a diluent and if appropriate in the presence of a reaction auxiliary, or when
b) N-methyl-3-(3-hydroxyphenyl)-2-methoximino-propionamide, of the formula (III ),

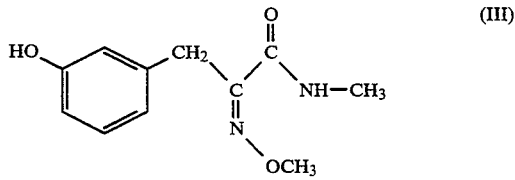
(III)

is acylated or alkylated with alkylating or acylating agents of the formula (IV)

(IV)

in which
R¹ and n have the abovementioned meaning and
E represents an electron-attracting leaving group,
if appropriate in the presence of a diluent and if appropriate in the presence of a reaction auxiliary.

Finally, it has been found that the new substituted oxime ether amides of the general formula (I) have a good activity against pests.

Surprisingly, the substituted oxime ether amides of the general formula (I) according to the invention show a considerably better activity against phytopathogenic fungi and insects than the substituted acrylic ester derivatives known from the prior art such as, for example, the compound methyl 3-methoxy-2-(2-methylphenyl)-acrylate or the compound methyl 3-methoxy-2-(2- phenoxyphenyl)-acrylate, which are similar compounds chemically and from the point of view of their action.

Formula (I) provides a general definition of the substituted oxime ether amides according to the invention. Preferred compounds of the formula (I) are those in which R represents aryl which has 6 to 10 carbon atoms and which is optionally monosubstituted or polysubstituted by identical or different substituents, suitable substituents being:

halogen, cyano, nitro, in each case straight-chain or branched alkyl, alkoxy, alkylthio, alkylsulphinyl or alkylsulphonyl, each of which has 1 to 6 carbon atoms, in each case straight-chain or branched alkenyl, alkinyl, alkenyloxy, alkinyloxy, alkenylthio or alkinylthio, each of which has 2 to 6 carbon atoms, in each case straight-chain or branched halogenoalkyl, halogenoalkoxy or halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl, halogenoalkinyl, halogenoalkenyloxy, halogenoalkinyloxy, halogenoalkenylthio or halogenoalkinylthio, each of which has 2 to 6 carbon atoms and 1 to 11 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl, each of which has 1 to 6 carbon atoms in the individual alkyl moieties, and also phenyl, phenoxy, phenylthio, phenylcarbonyl, phenylcarbonyloxy, phenylcarbonylamino, phenylcarbonyl-(N-alkyl)-amino, phenylaminocarbonyl, N-phenyl-N-alkyl-aminocarbonyl, phenylalkyl or phenylalkenyl, each of which has, where appropriate, up to 6 carbon atoms in the individual alkyl or alkenyl moieties and each of which is optionally monosubstituted or polysubstituted by identical or different substituents from the series comprising halogen and/or straight-chain or branched alkyl and/or alkoxy having 1 to 4 carbon atoms, and R furthermore represents a radical of the formula

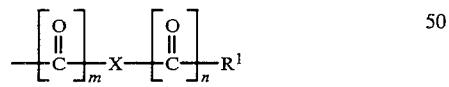

where $R^1$ represents straight-chain or branched alkyl having 1 to 6 carbon atoms, straight-chain or branched halogenoalkyl having 1 to 6 carbon atoms and 1 to 13 identical or different halogen atoms, in each case straight-chain or branched alkoxyalkyl or alkoxycarbonylalkyl, each of which has 1 to 6 carbon atoms in the individual alkyl moieties, or represents cycloalkyl or cycloalkylalkyl, each of which has 3 to 7 carbon atoms in the cycloalkyl moiety and, if appropriate, 1 to 6 carbon atoms in the straight-chain or branched alkyl moiety and each of which is optionally monosubstituted or polysubstituted by identical or different substituents, suitable cycloalkyl substituents in each case being: halogen and/or straight-chain or branched alkyl having 1 to 4 carbon atoms, $R^1$ furthermore represents aryl or arylalkyl, each of which has 6 to 10 carbon atoms in the aryl moiety and, if appropriate, 1 to 6 carbon atoms in the straight-chain or branched alkyl moiety and each of which is optionally monosubstituted or polysubstituted by identical or different substituents, or represents heterocyclyl or heterocyclylalkyl, each of which has 2 to 9 carbon atoms and 1 to 4 identical or different hetero atoms—in particular nitrogen, oxygen and/or sulphur—in the heterocyclyl moiety and, if appropriate, 1 to 6 carbon atoms in the straight-chain or branched alkyl moiety, and each of which is optionally monosubstituted or polysubstituted in the heterocyclyl moiety by identical or different substituents, suitable aryl substituents or heterocyclyl substituents in each case being those mentioned in the case of the substituent R, X represents oxygen or a radical of the formula N—$R^2$, $R^2$ represents hydrogen or straight-chain or branched alkyl having 1 to 6 carbon atoms, m represents a number 0 or 1 and n represents a number 0 or 1.

Particularly preferred compounds of the formula (I) are those in which

R represents aryl which has 6 to 10 carbon atoms and which is optionally monosubstituted to pentasubstituted by identical or different substituents, suitable substituents being:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched alkenyl, alkinyl, alkenyloxy, alkinyloxy, alkenylthio or alkinylthio, each of which has 2 to 5 carbon atoms, in each case straight-chain or branched halogenoalkyl, halogenoalkoxy or halogenoalkylthio, halogenoalkylsulphinyl or halogenoalkylsulphonyl, each of which has 1 to 4 carbon atoms and 1 to 9 identical or different halogen atoms, in each case straight-chain or branched halogenoalkenyl, halogenoalkinyl, halogenoalkenyloxy, halogenoalkinyloxy, halogenoalkenylthio or halogenoalkinylthio, each of which has 2 to 5 carbon atoms and 1 to 9 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl, each of which has 1 to 4 carbon atoms in the individual alkyl moieties, and also phenyl, phenoxy, phenylthio, phenylcarbonyl, phenylcarbonyloxy, phenylcarbonylamino, phenylcarbonyl-(N-alkyl)-amino, phenylaminocarbonyl, N-phenyl-N-alkyl-aminocarbonyl, phenylalkyl or phenylalkenyl, each of which has, where appropriate, up to 4 carbon atoms in the individual alkyl or alkenyl moieties and each of which is optionally monosubstituted or polysubstituted by identical or different substituents from the series comprising halogen and/or in each case straight-chain or branched alkyl and/or alkoxy, each of which has i to 3 carbon atoms, and R furthermore represents a radical of the formula

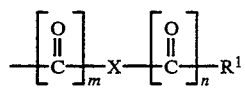

where
R¹ represents straight-chain or branched alkyl having 1 to 4 carbon atoms, or represents straight-chain or branched halogenoalkyl having 1 to 4 carbon atoms and 1 to 9 identical or different halogen atoms, or represents in each case straight-chain or branched alkoxyalkyl or alkoxycarbonylalkyl, each of which has 1 to 4 carbon atoms in the individual alkyl moieties, or represents cycloalkyl or cycloalkylalkyl, each of which has 3 to 6 carbon atoms in the cycloalkyl moiety and, if appropriate, 1 to 4 carbon atoms in the straight-chain or branched alkyl moiety and each of which is optionally monosubstituted to tetrasubstituted by identical or different substituents, suitable cycloalkyl substituents in each case being:
halogen and/or straight-chain or branched alkyl having 1 to 3 carbon atoms,
R¹ furthermore represents aryl or arylalkyl, each of which has 6 or 10 carbon atoms in the aryl moiety and, if appropriate, 1 to 4 carbon atoms in the straight-chain or branched alkyl moiety and each of which is optionally monosubstituted to pentasubstituted by identical or different substituents, or represents heterocyclyl or heterocyclylalkyl, each of which has 2 to 9 carbon atoms and 1 to 3 identical or different hereto atoms—in particular nitrogen, oxygen and/or sulphur—in the heterocyclyl moiety and, if appropriate, 1 to 4 carbon atoms in the straight-chain or branched alkyl moiety, and each of which is optionally saturated or unsaturated in the heterocyclyl moiety and each of which is optionally monosubstituted to pentasubstituted by identical or different substituents, suitable aryl substituents or heterocyclyl substituents being those mentioned in the case of the substituent R,
X represents oxygen or a radical of the formula N—R²,
R² represents hydrogen or straight-chain or branched alkyl having 1 to 4 carbon atoms,
m represents a number 0 or 1 and
n represents a number 0 or 1.
Very particularly preferred compounds of the formula (I) are those in which
R represents phenyl which is optionally monosubstituted to trisubstituted by identical or different substituents, suitable substituents being:
halogen, cyano, nitro, in each case straight-chain or branched alkyl, alkoxy, alkylthio, alkylsulphinyl or alkylsulphonyl, each of which has 1 to 3 carbon atoms, in each case straight-chain or branched alkenyl, alkinyl, alkenyloxy, alkinyloxy, alkenylthio or alkinylthio, each of which has 2 to 4 carbon atoms, in each case straight-chain or branched halogenoalkyl, halogenoalkoxy, halogenoalkylthio, halogenoalkylsulphinyl or halogenoalkylsulphonyl, each of which has 1 to 2 carbon atoms and 1 to 5 identical or different halogen atoms, in each case straight-chain or branched halogenoalkenyl, halogenoalkinyl, halogenoalkinyloxy, halogenoalkinyloxy, halogenoalkenylthio or halogenoalkinylthio, each of which has 2 to 3 carbon atoms and 1 to 5 identical or different halogen atoms, in each case straight-chain or branched alkylcarbonyl, alkoxycarbonyl, alkylcarbonyloxy, alkylcarbonylamino, alkylcarbonyl-(N-alkyl)-amino, aminocarbonyl, N-alkyl-aminocarbonyl, N,N-dialkylaminocarbonyl or alkoximinoalkyl, each of which has 1 to 3 carbon atoms in the individual alkyl moieties, and also phenyl, phenoxy, phenylthio, phenylcarbonyl, phenylcarbonyloxy, phenylcarbonylamino, phenylcarbonyl-(N-alkyl)-amino, phenylaminocarbonyl, N-phenyl-N-alkyl-aminocarbonyl, phenylalkyl or phenylalkenyl, each of which has, where appropriate, up to 3 carbon atoms in the individual alkyl or alkenyl moieties and each of which is optionally monosubstituted or polysubstituted by identical or different substituents from the series comprising halogen and/or in each case straight-chain or branched alkyl and/or alkoxy, having 1 to 3 carbon atoms, and
R furthermore represents a radical of the formula

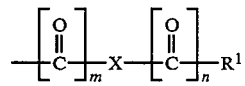

where
R¹ represents straight-chain or branched alkyl having 1 to 3 carbon atoms, or represents straight-chain or branched halogenoalkyl having 1 to 2 carbon atoms and 1 to 5 identical or different halogen atoms, in each case straight-chain or branched alkoxyalkyl or alkoxycarbonylalkyl, each of which has 1 to 3 carbon atoms in the individual alkyl moieties, or represents cyclopropyl, cyclopentyl, cyclohexyl, cyclopropylalkyl, cyclopentylalkyl or cyclohexylalkyl, each of which has, where appropriate, 1 to 3 carbon atoms in the straight-chain or branched alkyl moiety and each of which is optionally monosubstituted or disubstituted by identical or different substituents, suitable cycloalkyl substituents in each case being: fluorine, chlorine, bromine and/or straight-chain or branched alkyl having 1 to 3 carbon atoms,
R¹ furthermore represents phenyl or phenylalkyl which has, where appropriate, 1 to 3 carbon atoms in the straight-chain or branched alkyl moiety and each of which is optionally monosubstituted to trisubstituted by identical or different substituents, or represents heterocyclyl or heterocyclylalkyl which has, if appropriate, 1 to 3 carbon atoms in the straight-chain or branched alkyl moiety and each of which is optionally monosubstituted to trisubstituted by identical or different substituents and/or benzo-fused, particularly suitable heterocyclyl radicals being:
pyridinyl, pyrimidinyl, triazinyl, imidazolyl, triazolyl, pyrazolyl, thiazolyl, isothiazolyl, thiadiazolyl, oxazolyl, isoxazolyl and oxadiazolyl, and suitable phenyl or hetero cyclyl substitutents in each case being those mentioned in the case of the substituent R,
X represents oxygen or a radical of the formula N—R², $R^2$ represents hydrogen or straight-chain or branched alkyl having 1 to 3 carbon atoms, m represents a number 0 or 1 and n represents a number 0 or 1.

Reference is made to the individual compounds mentioned in the Preparation Examples.

If, for example, N-methyl-2-acetamido-3-[3-(4-methylphenyl)-phenyl]-acrylamide and O-methylhydroxylamine hydrochloride are used as starting materials, the course of the reaction of process (a) according to the invention can be represented by the following equation:

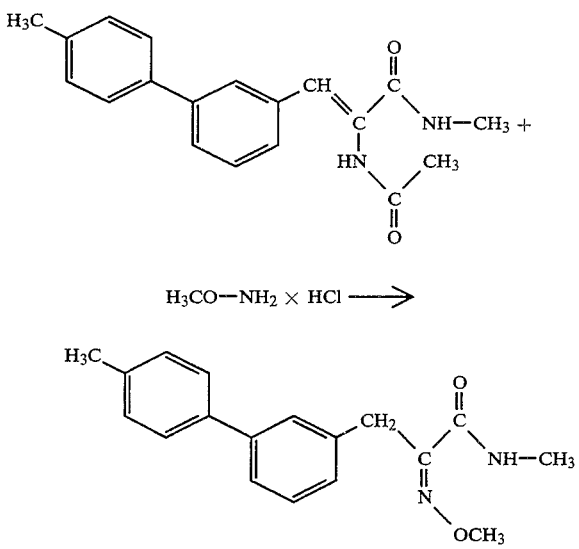

If, for example, N-methyl-3-(3-hydroxyphenyl)-2-methoximino-propionamide and 4-chlorobenzoyl chloride are used as starting materials, the course of the reaction of process (a) according to the invention can be represented by the following equation:

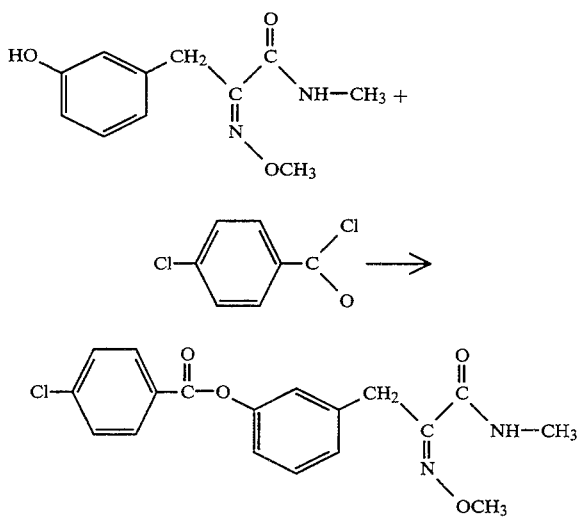

Formula (II) provides a general definition of the acrylamide derivatives required as starting materials for carrying out process (a) according to the invention. In this formula (II), R preferably represents those radicals which have already been mentioned in connection with the description of the substances of the formula (I) according to the invention as being preferred for these substituents.

The acrylamide derivatives of the formula (II) were hitherto unknown and are also a subject of the invention. They are obtained when aromatic aldehydes of the formula (V)

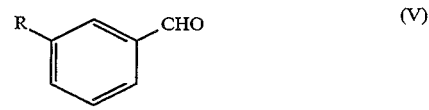

in which

R has the abovementioned meaning are reacted with N-acetylglycine at temperatures between 20° C. and 160° C. in the presence of acetic anhydride and sodium acetate and, if appropriate, in the presence of acetic acid, and by subsequently reacting, in a second step, the resulting azlactones of the formula (VI)

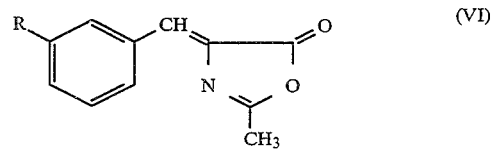

in which

R has the abovementioned meaning with methylamine at temperatures between 0° C. and 50° C., if appropriate in the presence of a diluent.

Aromatic aldehydes of the formula (V) are generally known compounds of organic chemistry or can be obtained in analogy to generally known processes.

The azlactones of the formula (VI) are known (compare, for example, DE 4,019,307).

N-Methyl-3-(3-hydroxyphenyl)-2-methoximino-propionamide of the formula (III), which is required as starting compound for carrying out process (b) according to the invention, was hitherto unknown and is also a subject of the invention.

It is obtained when 3-hydroxybenzaldehyde is first reacted, in a first step, with N-acetylglycine in the presence of acetic anhydride and sodium acetate at temperatures between 20° C. and 160° C., if appropriate in the presence of acetic acid, and the resulting azlactone of the formula (VIa)

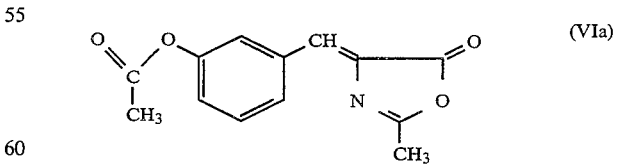

is subsequently reacted, in a second step, with methanol at temperatures between 0° C. and 50° C., if appropriate in the presence of a base such as, for example, sodium hydroxide, and subsequently in the presence of an acid such as, for example, hydrochloric acid, the resulting acrylic ester derivative of the formula (VIIa)

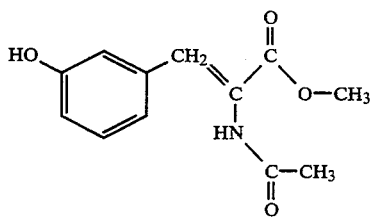

(VIIa)

is then reacted, in a third step, with an acid addition salt of O-methyl hydroxylamine analogously to the procedure of process (a) according to the invention, if appropriate in the presence of a diluent and if appropriate in the presence of a reaction auxiliary, and the resulting oximino ester of the formula (VIIIa)

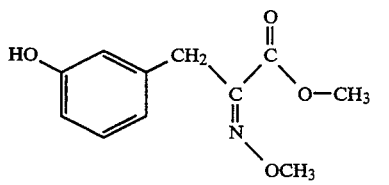

(VIIIa)

is finally reacted in a fourth step, with methylamine at temperatures between 100° C. and 150° C., if appropriate in the presence of a diluent such as, for example, tetrahydrofuran and, if appropriate, in the presence of a reaction auxiliary such as, for example, glacial acetic acid.

Formula (IV) provides a general definition of the alkylating or acylating agents furthermore required as starting materials for carrying out process (b) according to the invention. In this formula (IV), $R^1$ and n preferably represent those radicals and indices which have already been mentioned in connection with the description of the compounds of the formula (I) according to the invention as being preferred for this substituent and index. E represents a leaving radical customary in alkylating agents or acylating agents, preferably halogen, in particular chlorine, bromine or iodine, or, in the case of the alkylating agents, in each case optionally substituted alkylsulphonyloxy, alkoxysulphonyloxy or arylsulphonyloxy such as, in particular, methanesulphonyloxy, trifluoromethanesulphonyloxy, methoxysulphonyloxy, ethoxysulphonyloxy or p-toluenesulphonyloxy, or, in the case of acylating agents, also an alkanoyloxy radical such as, in particular, an acetoxy or propionyloxy radical.

The alkylating and acylating agents of the formula (IV) are generally known compounds of organic chemistry.

Suitable diluents for carrying out process (a) according to the invention are polar organic solvents or aqueous systems. The following diluents are particularly preferably used: alcohols such as, for example, methanol, ethanol or propanol, their mixtures with water, or pure water.

Suitable reaction auxiliaries for carrying out process (a) according to the invention are strong mineral acids such as hydrochloric acid, hydrobromic acid or sulphuric acid.

When carrying out process (a) according to the invention, the reaction temperatures can be varied within a substantial range. In general, the process is carried out at temperatures between 0° C. and 100° C., preferably at temperatures between 20° C. and 60° C.

For carrying out process (a) according to the invention, 1.0 to 3.0 moles, preferably 1.0 to 1.5 moles, of O-methylhydroxylamine and, if appropriate, 1.0 to 3.0 moles, preferably 1.0 to 1.5 moles, of reaction auxiliary are employed per mole of acrylamide derivative of the formula (II).

The reaction is carried out and the reaction products are worked up and isolated by known processes (compare, in this context, for example DE 4,019,307 or the Preparation Examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or sulphoxides such as dimethyl sulphoxide.

If appropriate, process (b) according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyl-dimethylammonium methylsulphate, dimethyl-$C_{12}$/$C_{14}$-alkylbenzylammonium chloride, dimethyl-$C_{12}$/$C_{14}$-alkylbenzylammonium bromide, tetrabutylammonium hydroxide, triethylbenzylammonium chloride, methyltrioctylammonium chloride, trimethylbenzylammonium chloride, 15-crown-5, 18-crown-6, or tris-[2-(2-methoxyethoxy)-ethyl]-amine.

Process (b) according to the invention is preferably carried out in the presence of a suitable reaction auxiliary. Suitable reaction auxiliaries are all customary inorganic and organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium t-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (b) according to the invention, the reaction temperatures can be varied with in a substantial range. In general, the process is carried out at temperatures between −20° C. and 100° C., preferably at temperatures between 0° C. and 60° C.

For carrying out process (b) according to the invention, 1.0 to 5.0 moles, preferably 1.0 to 1.5 moles of alkylating or acylating agent of the formula (IV) and, if appropriate, 1.0 to 5.0 moles, preferably 1.0 to 1.5 moles, of reaction auxiliary are generally employed per mole of N-methyl-3-(3-hydroxyphenyl)-2-methoximinopropionamide of the formula (III). The reaction is carried out and the reaction products are worked up and isolated by known processes (compare in this context for example DE 4,019,307 or the Preparation Examples).

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: for example, Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, per, nits treatment of above-ground parts of plants, of vegetative propagation stock and seeds, and of the soil.

In this context, the active compounds according to the invention can be employed with particular success for combating cereal diseases such as, for example, against the causative organism of powdery mildew of cereals on barley or wheat (*Erysiphe graminis*) or against the causitive organism of net blotch of barley (*Pyrenophora teres*) or against the causitive organism of leaf spot of barley or wheat (*Cochliobolus sativus*) or against the causitive organism of glume blotch of wheat (*Septoria nodorum*), or for combating diseases in fruit and vegetable growing such as, for example, against the causative organism of apple scab (*Venturia inaequalis*), or for combating rice diseases such as, for example, against the causitive organism of rice blast disease (*Pyricularia oryzae*) or against the causitive organism of rice stem blight (*Pellicularia sasakii*). In this context, the active compounds according to the invention not only show good protective properties, but also systemic activity. Besides, the active compounds according to the invention have a good in-vitro activity.

Moreover, the active compounds are also suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The abovementioned pests include:

From the order of the Isopoda, for example, *Oniscus asellus, Armadillidium vulgate* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus corpotis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, pseudococcus spp. Psylla spp*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Hellothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bissellleila, Tinea pellionella, Hofmannophila pseudospretella, Cacoecia podana, Capua reticulana, Choristoneura fumiferana, Clysia ambiguella, Homona magnanima* and *Tortfix viridana.*

From the order of the Coleoptera, for example, *Anobium punctatum, Rhizopertha dominica, Bruchidius obtectus, Acanthoscelides obtectus, Hylotrupes baJulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

The active compounds according to the invention are distinguished by a high insecticidal activity. They can be employed with particular success for combating plant-injurious insects, such as, for example against the larvae of the mustard beetles (*Phaedon cochleariae*) or against the caterpillars of the cabbage moth (*Plutella maculipennis*).

Depending on their particular physical and/or chemical properties the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids such as cephalins and lecithins, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as fungicides, the active compounds according to the invention can be present in the formulations as a mixture with other known active compounds, such as fungicides, insecticides, acaricides and herbicides, and as a mixture with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low-volume method or to inject the active compound preparation, or the active compound itself, into the soil. The seed of the plants can also be treated.

In the treatment of parts of plants, the active compound concentrations in the use forms can be varied within a substantial range. When the active compounds are used as fungicides, the concentrations are generally between 1 and 0.0001% by weight, preferably between 0.5 and 0,001%.

When the active compounds are used as fungicides in the treatment of seed, amounts of 0.001 to 50 g are generally required per kilogram of seed, preferably 0.01 to 10 g.

When the active compounds are used as fungicides in the treatment of the soil, the concentrations required are 0.00001 to 0.1% by weight, preferably from 0.0001 to 0.02%, at the site of action.

When used as insecticides, the active compounds according to the invention can also be present in their commercially available formulations and in the use forms prepared from these formulations as a mixture with other active compounds such as insecticides, attractants, sterilants, acaricides, nematicides, fungicides, growth-regulating substances or herbicides. The insecticides include, for example, phosphates, carbamates, carboxylates, chlorinated hydrocarbons, phenylureas, substances produced by microorganisms, and the like.

When used as insecticides, the active compounds according to the invention can furthermore be present in their commercially available formulations and in the use forms prepared from these formulations as a mixture with synergists. Synergists are compounds by which the action of the active compounds is increased, without it being necessary for the synergist added to be active itself.

When the active compounds are used as insecticides, the active compound content of the use forms prepared from the commercially available formulations can vary within wide limits. The active compound concentration of the use forms can be between 0.0000001 to 95% by weight of active compound, preferably between 0.0001 and 1% by weight.

They are used in a customary manner adapted to suit one of the use forms.

PREPARATION EXAMPLES

EXAMPLE 1

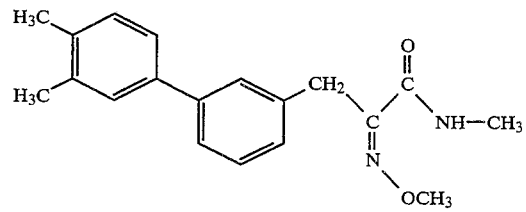

(Process a)

0.83 g (0.01 mol) of O-methylhydroxylamine hydrochloride in 10 ml of water and i ml (0.01 mol) of concentrated hydrochloric acid are added in succession at 60° C. to 3.22 g (0.01 mol) of N-methyl-2-acetamido-3-[3-(3,4-dimethylphenyl)-phenyl]-acrylamide in 200 ml of methanol, and the mixture is subsequently stirred for 39 hours at 60° C. For working-up, the reaction mixture is concentrated in vacuo, the residue is taken up in 100 ml of dichloromethane, the organic phase is washed twice using 50 ml portions of water, dried over sodium sulphate and concentrated in vacuo. The residue is chromatographed over silica gel (eluent: dichloromethane) and subsequently crystallised from n-hexane.

1.5 g (48% of theory) of N-methyl-3-[3-(3,4-dimethylphenyl)-phenyl]-2-methoximino-propionamide of melting point 80° C. are obtained.

Preparation of the Starting Compound

EXAMPLE II-1

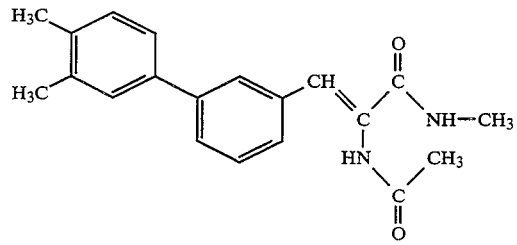

0.62 g (0.02 mol) of methylamine dissolved in 2 ml of methanol are added to 5.82 g (0.02 mol) of 2-methyl-4-[3-(3,4- dimethylphenyl)-phenylmethylidene]-2,3-dehydro-1,3-oxazolidin-5-one in 100 ml of toluene at room temperature, and the mixture is subsequently stirred for 18 hours at room temperature. For working-up, the precipitate which has separated out is filtered off with suction and dried.

5.6 g (87% of theory) of N-methyl-2-acetamido-3-[3-(3,4-dimethylphenyl)-phenyl]-acrylamide of melting point 224° C. are obtained.

EXAMPLE 2

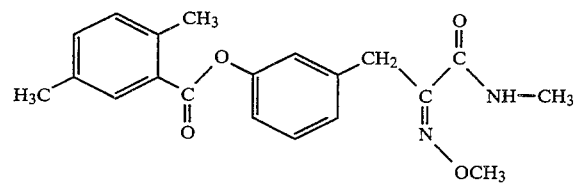

(Process b)

1.1 g (0.01 mol) of triethylamine and then dropwise and with stirring at room temperature, 1.7 g (0.01 mol) of 2,5-dimethylbenzoyl chloride are added to 2.2 g (0.01 mol) of N-methyl-3-(3-hydroxyphenyl)-2-methoximino-propionamide in 50 ml of ethyl acetate, and the mixture is stirred for a further 18 hours at room temperature after the addition has ended. For working-up, the mixture is washed once using 50 ml of water, dried over sodium sulphate and concentrated in vacuo, and the residue is crystallised with the aid of diisopropyl ether, filtered off with suction and dried.

2.6 g (73.4% of theory) of N-methyl-3-[3-(2,5-dimethylbenzoyloxy)-phenyl]-2-methoximino-propionamide of melting point 98° C. are obtained.

Preparation of the Starting Compound

EXAMPLE (III)

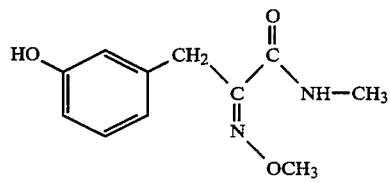

40 ml (0.4 mol) of 30 per cent strength aqueous methylamine solution and 4.8 g (0.08 mol) of glacial acetic acid are added in succession to 8.9 g (0.04 mol) of methyl 3-(3-hydroxyphenyl)-2-methoximino-propionate (compare, for example, DE-OS (German Published Specification) 4,019,307) in 120 ml of tetrahydrofuran, and the mixture is heated in the autoclave for 16 hours at 130° C. For working-up, the solvent is distilled off in vacuo, the residue is taken up in 150 ml of dichloromethane, and the organic phase is washed twice using 100 ml portions of water, dried over sodium sulphate and concentrated in vacuo. The residue is chromatographed over silica gel (eluent: dichloromethane) and subsequently recrystallised from diisopropyl ether.

3.4 g (38.6% of theory) of N-methyl-3-(3-hydroxyphenyl)-2-methoximino-propionamide of melting point 100° C. are obtained.

EXAMPLE 3

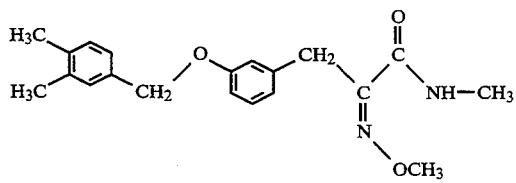

(Process b)

1.4 g (0.01 mol) of ground potassium carbonate, 2.0 g (0.01 mol) of 3,4-dimethylbenzyl bromide and a spatula-tip full of potassium iodide are added in succession to 2.2 g (0.01 mol) of N-methyl-3-(3-hydroxyphenyl)-2-methoximino-propionamide in 100 ml of acetone, and the mixture is stirred for 20 hours at 60° C. after the addition has ended. For working-up, the reaction mixture is concentrated in vacuo, the residue is taken up in 100 ml of dichloromethane, the mixture is washed twice using 50 ml portions of water, dried over sodium sulphate and concentrated in vacuo, and the residue is crystallised with the aid of diisopropyl ether, filtered off with suction and dried.

1.8 g (53% of theory) of N-methyl-3-[3-(3,4-dimethylbenzyloxy)-phenyl]-2-methoximino-propionamide of melting point 70° C. are obtained.

The following substituted oxime ether amides of the general formula (I) are obtained analogously and following the general preparation instructions:

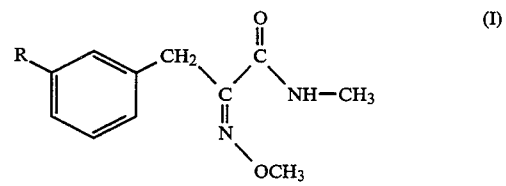

| Ex. No. | R | Physical properties |
|---|---|---|
| 4 | ![Cl-phenyl] Cl-C₆H₄- | m.p. 87° C. |
| 5 | 2,5-dichlorophenyl | m.p. 75° C. |
| 6 | $H_3CO-C(O)-$ | $n_D^{20} = 1.5396$ |
| 7 | benzyl-N=C(CH₂-O-)-CH=N (imidazole derivative) | m.p. 66° C. |
| 8 | 4-Cl-C₆H₄-C(O)-O- | m.p. 98° C. |
| 9 | $n\text{-}C_4H_9-O-C(O)-CH_2-O-$ | $n_D^{23} = 1.5078$ |
| 10 | 3-CH₃-C₆H₄-C(O)-O- | m.p. 100° C. |
| 11 | 3-CH₃-4-Cl-C₆H₃-C(O)-O- | m.p. 124° C. |
| 12 | 3,4-di-Cl-C₆H₃-C(O)-O- | m.p. 146° C. |

-continued

| Ex. No. | R | Physical properties |
|---|---|---|
| 13 | 3-(Cl₃C)-C₆H₄-C(=O)-O- | m.p. 92° C. |
| 14 | 2-CH₃-C₆H₄-CH₂-O- | m.p. 66° C. |
| 15 | 2,2-dichlorocyclopropyl-CH₂-O- | $n_D^{20}$ = 1.5476 |
| 16 | 2,6-dichloropyridin-3-yl-C(=O)-O- | m.p. 135° C. |
| 17 | 4-(F₃CO)-C₆H₄-CH₂-O- | $n_D^{20}$ = 1.5238 |
| 18 | 4-Cl-3-(F₃C)-C₆H₃-C(=O)-O- | m.p. 86° C. |
| 19 | 3-(n-C₄H₉-O)-C₆H₄-C(=O)-O- | m.p. 76° C. |
| 20 | i-C₃H₇-C(=N-N=)-O-CH₂-OCH₃ (1,3,4-oxadiazole) | — |
| 21 | 3-Cl-C₆H₄-CH₂-O- | $n_D^{23}$ = 1.5759 |
| 22 | 4-Cl-C₆H₄-CH₂-O- | $n_D^{23}$ = 1.5731 |
| 23 | 3,5-di-Cl-C₆H₃-CH₂-O- | $n_D^{23}$ = 1.5813 |
| 24 | 4,6-dichloro-2-phenoxy-1,3,5-triazin-yl-O- | m.p. 110° C. |
| 25 | 4,6-dichloro-1,3,5-triazin-2-yl-O- | m.p. 154° C. |
| 26 | (2,2-dichloro-1-methylcyclopropyl)-CH₂-O- | $n_D^{20}$ = 1,5483 |
| 27 | 1-benzyl-imidazol-2-yl-CH₂-O- | $n_D^{20}$ = 1,5650 |
| 28 | CH₃-(CH₂)₄-O-CO-CH₂-O- | $n_D^{20}$ = 1,5198 |
| 29 | (C₂H₅)₂N-CO-CH₂-O- | m.p. 78° C. |
| 30 | 3-phenyl-isoxazol-5-yl-CH₂-O- | m.p. 82° C. |
| 31 | (CH₃)₃C-O-CO-CH₂-O- | $n_D^{20}$ 1,5112 |
| 32 | C₆H₅-CH₂-O-CO-CH₂-O- | m.p. 56° C. |
| 33 | (CH₃)₂CH-CH₂-O-CO-CH₂-O- | $n_D^{20}$ = 1,5170 |
| 34 | 3,4-di-Cl-C₆H₃- | m.p. 90° C. (E-Isomers) |
| 35 | 2,6-dimethylmorpholin-4-yl-C(=O)-CH₂-O- | m.p. 90° C. (Z-Isomers) |
| 36 | 2,6-dimethylmorpholin-4-yl-C(=O)-CH₂-O- | $n_D^{20}$ = 1,5384 (E-Isomers) |
| 37 | morpholin-4-yl-C(=O)-CH₂-O- | m.p. 114° C. |

USE EXAMPLES

In the use examples which follow, the compounds listed below were employed as comparison substances:

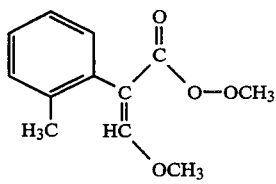

Methyl 3-methoxy-2-(2-methylphenyl)-acrylate (A)

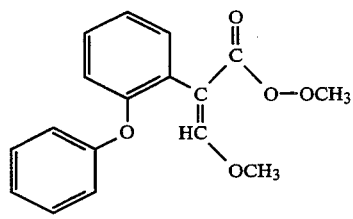

Methyl 3-methoxy-2-(2-phenoxyphenyl)-acrylate (both disclosed in EP 178,826).

(B)

EXAMPLE A

Venturia test (apples)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain for one day in an incubation cabin at 20° C. and 100% relative atmospheric humidity.

The plants are then placed in a greenhouse at 20° C. and a relative atmospheric humidity of approx. 70° C.

12 days after the inoculation, the test is evaluated.

In this test, a clearly superior activity compared with the prior art is shown, for example, by the compounds of the following Preparation Examples: 2, 3, 4, 5, 13, 14, 16 and 18.

EXAMPLE B

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis f.sp. hordei*.

The plants are placed in a greenhouse at a temperature of about 20° C. and at a relative atmospheric humidity of approx. 80% in order to promote the development of mildew pustules.

7 days after the inoculation, the test is evaluated.

In this test, a clearly superior activity compared with the prior art is shown, for example, the compounds of the following Preparation Examples: 1 and 5 show 100% activity at an active compound concentration of 250 ppm.

EXAMPLE C

Erysiphe test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist.

After the spray coating has dried on, the plants are dusted with spores of *Erysiphe graminis f.sp. tritici*.

The plants are placed in a greenhouse at a temperature of about 20° C. and at a relative atmospheric humidity of approx. 80% in order to promote the development of mildew pustules.

7 days after the inoculation, the test is evaluated.

In this test, a clearly superior activity compared with the prior art is shown, for example, by the compound of Preparation Example 1.

EXAMPLE D

Erysiphe test (barley)/curative
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.sp. hordei*. 48 hours after the inoculation, the plants are sprayed with the preparation of active compound until dew-moist.

The plants are placed in a greenhouse at a temperature of about 20° C. and at a relative atmospheric humidity of approx. 80% in order to promote the development of mildew pustules.

7 days after the inoculation, the test is evaluated.

In this test, a clearly superior activity compared with the prior art is shown, for example, by the compound of Preparation Example 1.

EXAMPLE E

Erysiphe test (wheat)/curative
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis f.sp. tritici*. 48 hours after the inoculation, the plants are sprayed with the preparation of active compound until dew-moist.

The plants are placed in a greenhouse at a temperature of about 20° C. and at a relative atmospheric humidity of approx. 80% in order to promote the development of mildew pustules.

7 days after the inoculation, the test is evaluated.

In this test, a clearly superior activity compared with the prior art is shown, for example, by the compound of Preparation Example 1.

EXAMPLE F

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by dipping into the active compound preparation of the desired concentration and infested with mustard beetle larvae (*Phaedon cochleariae*) while the leaves are still moist.

After the specified period of time, the destruction is determined in per cent. 100% denotes that all beetle larvae have been destroyed; 0% denotes that no beetle larvae have been destroyed.

In this test, for example, the following compounds of the Preparation Examples show superior activity compared with the prior art: 4 and 5.

EXAMPLE G

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by dipping into the active compound preparation of the desired concentration and infested with caterpillars of the cabbage moth (*Plutella maculipennis*) while the leaves are still moist.

After the specified period of time, the destruction is determined in per cent. 100% denotes that all caterpillars have been destroyed; 0% denotes that no caterpillars have been destroyed.

In this test, for example, the following compounds of the Preparation Examples show superior activity compared with the prior art: 4 and 5.

I claim:

1. An oxide either amide of the formula (I):

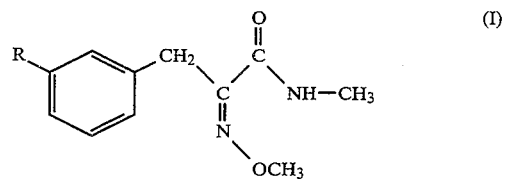

wherein
R represents phenyl, naphthyl, or phenyl or naphthyl monosubstituted to polysubstituted by identical or different substitutents selected from the group consisting of halogen, cyano, nitro, in each case straight-chain or branched alkyl, alkoxy, alkylthio, alkylsulphinyl or alkylsulphonyl, each of which has 1 to 6 carbon atoms, in each case straight-chain or branched alkenyl, alkynyl, alkenyloxy, alkynyloxy, alkenylthio or alkynylthio, each of which has 2 to 6 carbon atoms, in each case straight-chain or branched halogenoalkyl, halogenoalkoxy or halogenoalkylthio, halogenoalkylsulphinyl or halogenoalkylsulphonyl, each of which has 1 to 6 carbon atoms and 1 to 13 identical or different halogen atoms, in each case straight-chain or branched halogenoalkenyl, halogenoalkynyl, halogenoalkenyloxy, halogenoalkynyloxy, halogenoalkenylthio or halogenoalkynylthio, each of which has 2 to 6 carbon atoms and 1 to 11 identical or different halogen atoms, in each case straight-chain or branched alkylcarbonyl, alkoxycarbonyl, alkylcarbonyl-(N-alkyl)-amino, aminocarbonyl, N-alkylaminocarbonyl, N,N-dialkylaminocarbonyl or alkoximinoalkyl, each of which has 1 to 6 carbon atoms in the individual alkyl moieties, and phenyl, phenoxy, phenylthio, phenylcarbonyl, phenylcarbonyloxy, phenylcarbonylamino, phenyl carbonyl-(N-alkyl)-amino, phenylaminocarbonyl, N-phenyl-(N-alkyl)aminocarbonyl, phenylalkyl or phenylalkenyl, each of which has, where appropriate, up to 6 carbon atoms in the individual alkyl or alkenyl moieties and each of which is unsubstituted or monosubstituted to polysubstituted by identical or different substituents selected from the group consisting of halogen, straight-chain or branched alkyl or alkoxy, each of which has 1 to 4 carbon atoms.

2. A compound according to claim 1, wherein such compound is N-methyl-3-[3-(3,4-dimethylphenyl)-phenyl]-2-methoximino-propionamide of the formula

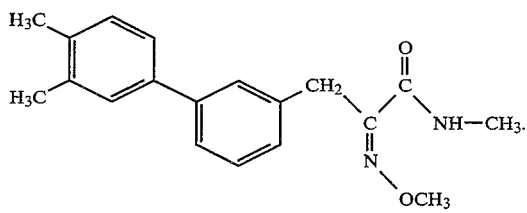

3. A pesticidal composition comprising a pesticidally effective amount of a compound according to claim 1 and a diluent.

4. A method of combatting pests which comprises applying to such pests or a pest habitat a pesticidally effective amount of a compound according to claim 1 and a diluent.

* * * * *

UNITED STATES PATENT AND TRADEMARK OFFICE
CERTIFICATE OF CORRECTION

PATENT NO. : 5,354,779
DATED : October 11, 1994
INVENTOR(S) : Wolfgang Kramer, et al.

It is certified that error appears in the above-indentified patent and that said Letters Patent is hereby corrected as shown below:

Column 23, line 67,   delete "either" and substitute --ether--

Signed and Sealed this

Fifth Day of May, 1998

Attest:

BRUCE LEHMAN

Attesting Officer   Commissioner of Patents and Trademarks